(12) United States Patent
Maurer

(10) Patent No.: US 8,728,214 B2
(45) Date of Patent: May 20, 2014

(54) GAS TRANSFER DEVICE AND USE OF A STRUCTURED MEMBRANE

(75) Inventor: Andreas Maurer, Tuebingen (DE)

(73) Assignee: Novalung GmbH, Talheim (DE)

( * ) Notice: Subject to any disclaimer, the term of this patent is extended or adjusted under 35 U.S.C. 154(b) by 491 days.

(21) Appl. No.: 13/061,821

(22) PCT Filed: Sep. 3, 2009

(86) PCT No.: PCT/EP2009/006403
§ 371 (c)(1),
(2), (4) Date: Jun. 3, 2011

(87) PCT Pub. No.: WO2010/025926
PCT Pub. Date: Mar. 11, 2010

(65) Prior Publication Data
US 2011/0226686 A1    Sep. 22, 2011

(30) Foreign Application Priority Data
Sep. 3, 2008  (DE) .......................... 10 2008 045 621

(51) Int. Cl.
*B01D 53/22*    (2006.01)
*B01D 59/12*    (2006.01)
*A61M 1/00*    (2006.01)

(52) U.S. Cl.
USPC .................................................. 96/4; 422/48

(58) Field of Classification Search
USPC .................................................. 96/4; 422/48
See application file for complete search history.

(56) References Cited

U.S. PATENT DOCUMENTS

| 4,111,659 A | 9/1978 | Bowley |
| 5,958,616 A | 9/1999 | Salinas et al. |
| 2004/0060823 A1 | 4/2004 | Carson et al. |
| 2005/0232811 A1 | 10/2005 | Autschbach et al. |
| 2009/0098017 A1* | 4/2009 | Celik-Butler et al. .......... 422/48 |

FOREIGN PATENT DOCUMENTS

| DE | 3207 174 | 9/1983 |
| DE | 6980765 | 1/2003 |
| DE | 101 39 830 | 2/2003 |
| DE | 103 11 950 | 9/2004 |
| DE | 103 32 789 | 2/2005 |
| DE | 10 2006 011 471 | 9/2006 |
| EP | 0 121 445 | 10/1984 |
| EP | 1847594 | 10/2007 |
| JP | 11-104468 | 4/1999 |
| WO | WO 80/00920 | 5/1980 |
| WO | WO 02/32558 | 4/2002 |
| WO | WO 02/076529 | 10/2002 |

* cited by examiner

*Primary Examiner* — Robert A Hopkins
(74) *Attorney, Agent, or Firm* — Seed IP Law Group PLLC

(57) ABSTRACT

The invention relates to a gas transfer device comprising at least two chambers and at least one gas-permeable and liquid-impermeable membrane, wherein the chambers are separated from one another by the membrane(s), and wherein the membrane(s) is/are structured on at least one side and channels and/or branching structures, in particular branched pathways, are formed on the membrane by this structure, the walls of which have a spacing of ≤500 μm, preferably of ≤350 μm, and more preferably of ≤150 μm, and the proportion of the membrane surface area which comprises channels and/or branching structures having this spacing constitutes at least 50% of the total surface area of the membrane.

34 Claims, 4 Drawing Sheets

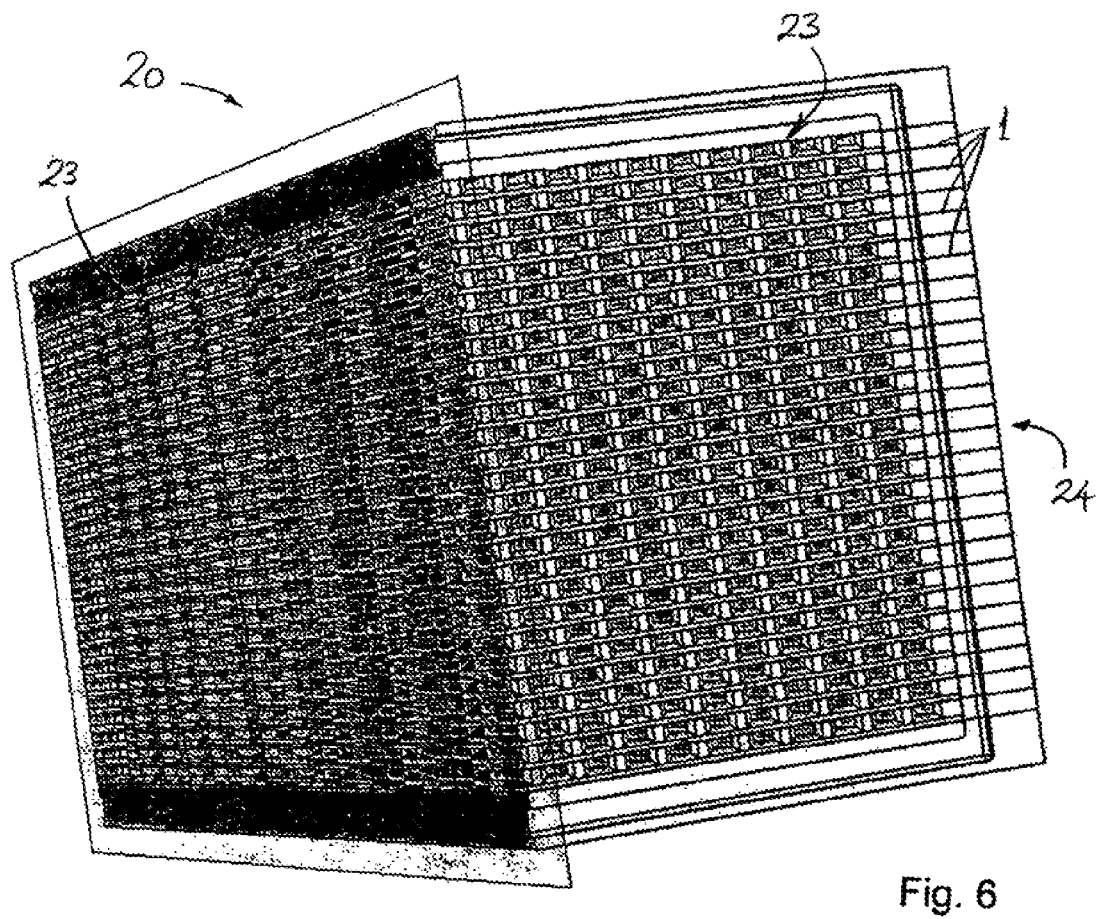
Fig. 6
Fig. 7
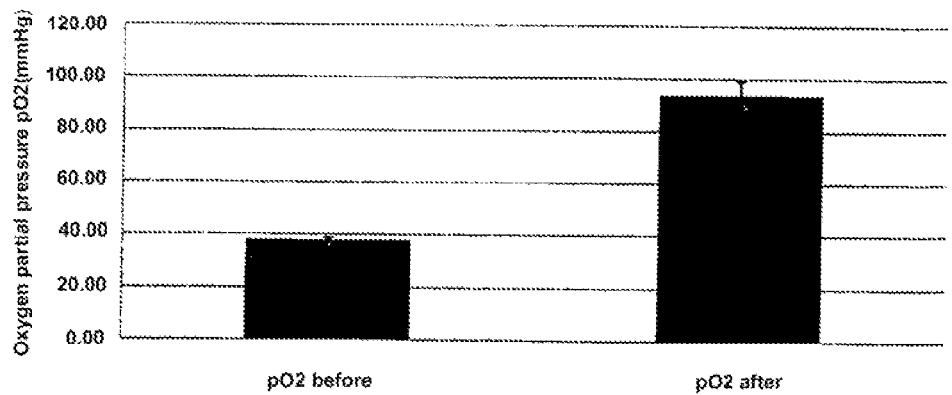

GAS TRANSFER DEVICE AND USE OF A STRUCTURED MEMBRANE

This application is a National Stage of PCT/EP2009/006403, filed Sep. 3, 2009 which claims priority to German Patent No. 10 2008 045 621.7, filed Sep. 3, 2008, the disclosures of which are incorporated herein by reference in their entirety.

BACKGROUND OF THE INVENTION

The invention relates to a gas transfer device with a specifically structured membrane, wherein thanks to its structuring the membrane permits particularly effective gas exchange, in particular between a liquid phase and a gaseous phase.

Gas transfer devices are used in many fields of technology. Such devices are either gassing or degassing devices, in which one or more gases pass from one medium into another, or gas exchange devices which permit mutual exchange of one or more gases between two media. Gas transfer devices are used, for example, in chemical process engineering, where they serve to supply gases for gas/liquid or gas/solid reactions. They may, however, also be used for gas separation or gas purification, by a gas not being introduced, but instead stripped out of a gas mixture or another reaction mixture.

Gas transfer devices are moreover likewise used in biotechnology and medicine. Their most important place of use in biotechnology is use in culturing reactors. Gas transfer devices are used to supply cell cultures in a specific and controlled manner with the gases necessary for a certain culture or excreted gases are removed from the nutrient medium. Gas transfer devices are also used in medicine. In this case, the most important intended use is to oxygenate the blood while simultaneously removing carbon dioxide from the blood. Such measures are required, for example, in diverse surgical operations and in the treatment of various lung diseases.

Causing as they do 9 million deaths per year, lung diseases are in third place in the WHO's cause of death statistics. Lung transplantation is currently the only therapeutic option with long-term effectiveness for patients with end-stage functional lung disease. There is at present no other medical solution for the long-lasting replacement of lung function. There is therefore in particular a significant requirement for long-lasting, artificial lung replacement methods which can be used in patients with chronic lung disease who cannot be considered for lung transplantation. There is moreover likewise a requirement for lung replacement devices which can be used in patients awaiting lung transplantation. Waiting times are currently so long that some 80% of patients die before receiving the lung transplantation which is medically indicated. Suitable lung replacement devices which can be used over extended periods could be of assistance here.

Gasifying devices were developed for such purposes as long ago as the 1950s. These devices, known as oxygenators, i.e. oxygen-gasifying devices, have since undergone continuous development and their functionality is still today being further improved.

The prototype of such an oxygenator was a film oxygenator in which blood conveyed by a roller pump through screens was oxygenated in an almost pure oxygen environment. However, large-area direct contact with oxygen led to denaturation of plasma proteins, a decisive drawback to the use of the film oxygenator.

The "bubble" oxygenator was then developed, blood being oxygenated with gas bubbles in a column of blood. The level of saturation is adjusted by varying the gas flow. Gas exchange here proceeds directly on the surface of the gas bubbles. The most serious problem of the bubble oxygenator was and remains the foaming of the blood which occurs during oxygenation, which can lead to microembolisms in the body. Subsequent defoaming methods are therefore required, making this method complex and costly. Examples of bubble-type oxygenators are described inter alia in DE 22 08 868, DE 23 14 644, DE 23 32 445 and DE 30 01 018.

Shortly after the bubble oxygenator was developed, a membrane oxygenator was used for the first time as long ago as 1956. In the membrane oxygenator, the gas phase is separated from the blood phase by a membrane. Gas exchange proceeds at the gas-permeable membrane primarily by diffusion due to partial pressure differences between the gases involved. The membranes may here take the form of flat membranes or of capillary or fibre membranes. Two types of membrane oxygenators from the more recent prior art are described, for example, in U.S. Pat. No. 5,137,531 and U.S. Pat. No. 6,682,698. One general disadvantage of membrane oxygenators which operate by diffusion is, however, that large membrane areas must be provided in order to achieve effective mass exchange between blood and oxygen in a specific time. Diffusion through the membrane may here by influenced by increasing oxygen pressure or by modifying the flow characteristics of the blood. It is, however, fundamentally really difficult to strike a compromise between potential blood damage, tendency towards thrombosis and effective gas exchange.

While very good diffusion may indeed be achieved in the fibre membrane oxygenators which are predominantly in use today thanks to the large total surface area of the membrane, a drawback for this oxygenator is the costly and complex manufacture of the fibres. A further disadvantage of currently used oxygenators is their only very short useful life. A prior art oxygenator may accordingly be used for only a few days, for at most up to a month. Long-term use, as would in particular be desirable for patients with chronic lung failure, cannot however be carried out satisfactorily.

The disadvantages stated by way of example for the oxygenators used in medicine occur likewise in gas transfer devices which are used for process engineering purposes in chemistry and biotechnology.

DESCRIPTION OF THE INVENTION

The object of the present invention is accordingly to provide improved gas transfer devices which may be used in chemistry, biotechnology and medicine, in particular for gassing or for gas exchange in the blood. In particular, the following invention is intended to provide a gas transfer device having improved gas transfer through the membrane and having an increased useful life.

This object is achieved according to the invention by the gas transfer device stated according to the main claim, which comprises at least two chambers and at least one gas-permeable and liquid-impermeable membrane, the chambers being separated from one another by the membrane(s), and which are characterised in that the membrane(s) is/are structured on at least one side and channels and/or branching structures are formed on the membrane by said structuring or structure, the walls of which have a spacing of ≤500 µm, preferably of ≤250 µm, and more preferably of ≤150 µm, and the proportion of the membrane surface area which comprises channels and/or branching structures having this spacing constitutes at least 50% of the total surface area of the membrane.

The gas transfer device according to the invention is distinguished by a particularly advantageously structured membrane provided with gas exchange channels and/or branching structures. In this connection, "branching structures" should be understood to be in relation to the contact faces and the resultant pathways for a liquid or gaseous phase on that side of the membrane.

In a preferred embodiment of the invention, at least one, and preferably each one, of the at least two chambers of the gas transfer device should be constructed as a through-flow chamber. The "branching structures" in the structuring or structure of the membrane are therefore branching or winding pathways for flow of the liquid or gaseous phase over the respective side of the membrane or through the chamber. The branching structures may for example arise from points in the membrane structure which stand as obstructions in the direction of flow and cause deflection and/or splitting or subdivision of flow through the respective chamber. For this purpose, the membrane is structured on at least one side in such a manner that the walls of the structure project or stand out from a plane of the membrane and/or project or extend into the respective adjacent chambers. These walls may for example be flowed around by the liquid or gaseous phase in the chamber. These walls of the structure, with which at least one side of the membrane is provided, form for example projections which may have geometric shapes, such as for example cuboids, rhomboids, cylinders or posts, and give rise to a branching structure of that side of the membrane. These walls may likewise form channels (for example branched channels) which guide the liquid or gaseous phase in the chamber over that side of the membrane.

The structuring or structure according to the invention of the membrane enables improved mass transfer (in particular due to improved diffusion characteristics) through the membrane, without, however, requiring the membrane to be of large dimensions, as provided in the prior art. This is due, on the one hand, to the fact that the structuring creates a larger surface area, which has a positive impact on gas transfer. On the other hand, the walls of the channels and/or branching structures formed on the membrane by the structuring have a small spacing, whereby diffusion through the membrane is accelerated. The small spacing of the channels and/or branching structures here brings about a distinct reduction in flow resistance. This is of particular significance for liquids such as for example biological liquids. When using blood, the "Fåhrus-Lindqvist effect" leads to the formation of a film of blood plasma on the walls, on which the cells slide through the channels and/or branching structures structured according to the invention.

According to the invention, the at least one gas-permeable and liquid-impermeable membrane of the gas transfer device according to the invention, which separates the chambers from one another, is typically structured on at least one side. When liquids are used in the chamber(s), it is preferably the side of the membrane which faces the liquid which is structured. The positive characteristics (for example reduction of flow resistance) of a structured membrane on gas transfer are particularly clear in the case of liquids.

According to the invention, at least one and preferably each of the chambers is formed at least in part by the membrane or by the membrane structure. In other words, in a preferred embodiment of the invention, each chamber is at least in part bounded or enclosed by the membrane.

In a preferred embodiment of the invention, the at least two chambers comprise a first chamber for receiving or for through-flow of a biological liquid and a second chamber for receiving or for through-flow of a gas. The channels and/or branching structures formed by the structuring thus serve for the transfer of gas molecules between the gas and the biological liquid.

In a further preferred embodiment of the gas transfer device according to the invention, the first chamber is subdivided into a plurality of chambers, such that the device comprises a plurality of first chambers which are separated from the second chamber by a gas-permeable and liquid-impermeable membrane. The second chamber is likewise preferably subdivided into a plurality of chambers, such that the device comprises a plurality of second chambers which are separated from the first chamber(s) by a gas-permeable and liquid-impermeable membrane. The plurality of first chambers may be arranged next to one another in one or more rows, and/or one above the other in a plurality of layers. In similar manner, the plurality of second chambers may be arranged next to one another in one or more rows and/or one above the other in a plurality of layers. Furthermore, a lengthwise orientation of the first chamber(s) may extend, for example, crosswise and preferably at right angles to a lengthwise orientation of the second chamber(s). Each of the first chambers is thus preferably constructed for through-flow from an inlet to an outlet in a direction contrary or crosswise to the general direction of flow of the second chamber(s). Similarly, each of the second chambers is preferably constructed for through-flow from an inlet to an outlet in a direction contrary or crosswise to the general direction of flow of the first chamber(s).

According to the invention, the membrane may consist of an organic or an inorganic material or comprise such a material. Inorganic membrane materials include glass, ceramics (for example aluminium oxide, titanium dioxide or zirconium oxide), metal, silicone or carbon. Organic membrane materials include in particular polymer materials such as for instance polyacrylamides, polyacrylonitriles, polyamides, polybenzimidazoles, polybutadienes, polycarbonates, polydimethylsiloxanes, polyether sulfones, polyether imides, polyolefins, polyethylene terephthalates, polymethyl methacrylate, polymethylpentene, polyphenylene oxide, polystyrene, polysulfones, polyvinyl alcohol, polyvinyl chloride, polyvinylidene fluoride, other halogenated hydrocarbons and cellulose and cyclic olefin copolymers (COC). Organic membrane materials may comprise either the pure polymer, a polymer composite (i.e. a mixture of different polymers or copolymers) or polymer multilayers (i.e. polymer laminates).

In a preferred embodiment of the present invention, the membrane material is an organic material selected from the above-stated materials. Still more preferably, the membrane material is a polymer, a polymer composite or a polymer multilayer of the stated materials.

In a further preferred embodiment of the invention, the polymer is a polyolefin, such as for example polyethylene, polypropylene, polybutadiene or polypentene or methyl variants thereof. Most highly preferably, the membrane material consists of or comprises polymethylpentene. PDMS may, however, also be used.

A membrane material which is particularly suitable in this connection is the Mitsui Chemicals methylpentene polymer distributed under the product name TPX™. In addition to many advantageous characteristics (for example good biocompatibility), TPX™ is distinguished by particularly high oxygen permeability (for example 47,000 ml/m$^2$ per hour at 24 atm, 25° C., 90% relative humidity (RH), and 25 μm membrane thickness; i.e. an oxygen permeability of 47,000 ml/m$^2$ per 24 hours (24 h) per bar of pressure difference (i.e. 47,000 ml/m$^2$·24 h·bar) at 25° C., 90% relative humidity (RH) and a membrane thickness of 25 μm). TPX™ additionally exhibits low moisture permeability of 110 g of water per m$^2$, within 24 h at 40° C. and 90% relative humidity (RH) and low nitrogen permeability. TPX™ is therefore particularly suitable as a membrane material for the gas transfer device according to the invention, in particular for applications relating to oxygen transfer, for example for oxygenating blood.

Depending on the membrane material selected, there are various options for producing structured membranes or for structuring pre-existing membranes. The standard method for producing both organic and inorganic membranes is sintering, it being possible for the sintered material in turn to be manufactured by a plurality of methods, such as pressing methods, extrusion, film casting, settling methods and sol-gel methods. There is a range of further production processes for organic membranes, such as for example drawing (stretching a polymer at right angles to the direction of extrusion), the nuclear track method (radioactive irradiation with subsequent etching), the phase inversion method (precipitation reaction) and foaming (pore formation by $CO_2$ expansion). The industrial effort involved in producing organic membranes is generally lower than that for inorganic membranes. The membrane used may be produced or structured using any one of the stated or also other methods known from the prior art.

The membrane is preferably structured by lithographic methods, in particular using the LIGA technique. LIGA (abbreviation for the German terms for the method steps lithography, electroplating and replication moulding) is a method which is based on a combination of deep lithography, electroplating and microreplication moulding. The LIGA method was developed in the early 1980s in the course of development of the separation nozzle method for uranium enrichment to permit the manufacture of extremely small separation nozzles (E. W. Becker et al., Naturwissenschaften 69, 520-523 (1982)). The method permits the production of microstructures of minute size from various materials such as plastics, metal or ceramics (E. W. Becker et al., Microelectronic Engineering, 4, 35-56 (1986)). In particular, LIGA technology is also used in the field of microsystems engineering.

Depending on the radiation used in the lithography method, a distinction is drawn between X-ray LIGA and UV LIGA. The LIGA method typically consists of the following steps, which are carried out in succession: a layer up to 1 mm in thickness of a plastics material sensitive to X-rays or UV light (for example PMMA) is firstly placed on a base plate with an electrically conductive outer layer. Deep-lithographic structuring then proceeds by exposing a resist. The exposed zones are subsequently dissolved away using a suitable developer, leaving behind a negative of the metal structure which is to be produced in the electroplating step. In a subsequent electroplating method, a metal is deposited on the substrate in those zones in which the resist has been removed during development. The resist is subsequently dissolved way, leaving behind the deposited metal structure. This metal structure serves as a replication moulding tool for replication moulding techniques such as hot stamping and injection moulding, with which in particular organic membranes (for example of plastics) may be produced. In addition to hot stamping and injection moulding, it is also possible to use a roll-to-roll method or vacuum thermoforming for replication moulding. Further examples of techniques used for mould construction are micro-precision milling and ultra-precision milling.

According to the invention, the membrane used in the gas transfer device is structured on at least one side, the structuring preferably being obtainable using micro-injection moulding or hot stamping methods. In a further embodiment, the membrane is structured on both sides, this likewise preferably being obtainable using injection moulding or hot stamping methods.

The LIGA method is a technique which has not hitherto been used for producing structured membrane materials, it enabling the manufacture of products inexpensively and in large numbers. The present invention therefore likewise relates to a method for producing structured membranes by the LIGA method and to the membranes obtained by said method.

The membranes are structured in the micrometer range. According to the invention, the structuring forms channels and/or branching structures on the membrane, the walls of which have a spacing of ≤500 µm, preferably of ≤350 µm, more preferably of ≤150 µm, more highly preferably of ≤100 µm, and still more highly preferably of ≤80 µm. The dimension or height of these walls, in particular from the plane of membrane, is typically of the same order of magnitude as the spacing and is preferably in the range from 10-350 µm, more preferably in the range from 10-200 µm, and still more preferably in the range from 10-100 µm. According to the invention, the proportion of the membrane surface area which comprises channels and/or branching structures constitutes ≥50%, more highly preferably ≥60%, still more preferably ≥70% of the total surface area of the membrane.

The geometry of the structures on the membrane may be varied at will. Channels and/or branching structures which for example imitate the capillary structure of natural lung may accordingly be used as structures on the membrane.

Such channels and/or branching structures may also be obtained by structuring the membrane with various geometric shapes. Examples of advantageous geometric shapes are rhombuses, quadrilaterals, polygons and circles. The channels may for example be straight, but they may likewise be non-linear, for example assuming a sinuous shape or a mixer structure.

As has already been described, the membrane is provided with projecting, raised zones by the structuring. These zones have a preferred height of approx. 1 to 100 µm, preferably of approx. 5 to 50 µm, more highly preferably of approx. 10 to 30 µm and most highly preferably of approx. 10 to 20 µm.

The resultant channels and/or branching structures on the membrane may either be entirely composed of through-passages and enable constant flow of the medium, or they may however be only blind branches, into which the medium penetrates and (optionally after gas transfer) comes back out again the same way. The membrane is preferably predominantly provided with channels, still more highly preferably predominantly with channels and branching structures.

According to the invention, the channels on the membrane constitute through-passages for a medium, such that the medium may slide through the channels in parallel, antiparallel or in another manner (such as for example in undulating manner) relative to the inflow direction into the chamber. In contrast, branching structures according to the invention are branches which a medium may enter, but, as in a dead end street, not leave the branch again at a point other than the point of entry. The branching structures may be arranged parallel or perpendicular relative to the inflow direction into the chamber. They may also assume any desired angle between a parallel or perpendicular arrangement, i.e. an angle of 0° to 90°. The branching structures are preferably arranged at an angle of approx. 10° to 80°, more highly preferably of approx. 20° to 70°, still more preferably of approx. 30° to 60° and most highly preferably of approx. 40° to 50°, relative to the inflow direction. In such an arrangement of branching structures relative to the inflow direction into the chamber, the entrances to the branching structures are located on the side facing toward the main flow. Inflow into the branching structures here proceeds parallel, perpendicular or at one of the above-stated angles to the main flow. An arrangement of the branching structures relative to the inflow direction is likewise conceivable, which creates an arrangement between a perpendicular and parallel arrangement, such that inflow into the branching structures proceeds substantially antiparallel (i.e. antiparallel or at a any desired angle between antiparallel and perpendicular influx) to the main flow.

It has proved particularly advantageous for the surface area available for the channels and/or branching structures to constitute more than 50% of the total surface area of the membrane. This proportion may readily be calculated mathematically, by relating the difference value (in m²) between the total surface area of membrane and the surface area which is occupied by structures to the value for the total surface area (in m²).

The membrane used in the gas transfer device according to the invention may consist of any desired materials which exhibit good gas permeability. Gas permeability values are deemed to be good, for example, at values of above 100 ml/m², preferably above 1,000, more highly preferably above 5,000, still more preferably above 10,000 and most highly preferably above 20,000 ml/m² per hour at 24 atm (i.e. above 20,000 ml/m² within 24 h at ambient pressure), and at 25° C., 90% relative humidity (RH) and a material thickness of approx. 30 µm, depending on the desired purpose with regard to the particular desired gas (in particular for example oxygen or carbon dioxide). The membrane is furthermore typically substantially liquid-impermeable, i.e. it has a moisture permeability of <1,000, preferably of <500, more highly preferably of <100 and still more preferably of <10 g/m² (i.e. $gH_2O/m^2$) in 24 h, 40° C., 90% RH.

The (gas) permeable membrane may on the one hand be a porous membrane, i.e. a membrane which comprises discrete pores. On the other hand, the membrane may be a homogeneous solubility membrane without discrete pores, in which mass transfer proceeds by dissolution of the permeate (i.e. gas) in the polymer while separation proceeds on the basis of different levels of solubility in the polymer. The membrane is preferably a non-porous permeable membrane. Gas exchange may proceed by convective and diffusive mass exchange. Gas exchange is preferably diffusive and is determined by the difference in gas concentration on the two sides of the membrane.

In one specific embodiment of the present invention, the membrane is substantially selectively permeable to oxygen and/or carbon dioxide. Depending on the place of application of the gas transfer device according to the invention, the membrane may be particularly highly permeable to specific gases while having limited permeability to other gases. For example, when the gas transfer device is used for gas exchange in blood, good permeability to oxygen and/or carbon dioxide is of significance (see the above-stated permeability values).

In another specific embodiment, the membrane is impermeable or only slightly permeable to nitrogen. For example, for use in gas exchange, it is advantageous for the membrane to be only slightly permeable to nitrogen. In this case, air (instead of pure oxygen) may be used for gassing the blood.

For other applications of the gas transfer device according to the invention, the membrane will exhibit good permeabilities to other gases. For example, when used as or for reactors (for example bioreactors), the membrane may exhibit good permeability to one or more gases selected from $N_2$, $O_2$, $CO_2$, $H_2$, $NH_3$, $H_2S$, $CH_3$ or other hydrocarbons, or also other gases (for example noble gases). Membrane permeability to specific gases for use of the gas transfer device according to the invention in chemistry, for example for gas purification, gas separation or for reactions, depends on the nature of the gas to be isolated or purified or on the nature of the gas supplied to or removed from the reaction.

It is within the discretion of a person skilled in the art to select a membrane material having the suitable specific permeability to a specific gas or specific gases in the desired use of the gas transfer device according to the invention. Permeability values for many membrane materials are known from the prior art.

According to the invention, membrane thickness amounts to approx. 1-200 µm, preferably in the range from approx. 5-200 µm, more preferably approx. 10-100 µm, more highly preferably approx. 20-50 µm. The thickness is here the thickness of the membrane without the projecting zones obtained by structuring.

Due to the slight thickness of the membrane, it may be necessary to strengthen the membrane by a suitable support material. The membrane is preferably strengthened by a support material selected from the group consisting of porous foams, ceramics, polymers optionally also a supporting layer of TPX.

According to a further embodiment of the present invention, the membrane may also take the form of a membrane stack. The use of membrane stacks typically has at least two advantages over the use of single membranes. On the one hand, efficiency is increased, as a greater surface area is available for gas exchange. On the other hand, membrane stacks are also stronger than single membranes. Conversely, in applications which entail a compact design of the gas transfer device according to the invention, for example as a result of miniaturisation, it is more highly preferred to select a membrane instead of membrane stacks.

Membranes can be stacked automatically or by hand. The membranes may here either be laid parallel one on top of the other or be staggered relative to one another by a specific angle. Particularly preferred membrane stacks are those which are staggered relative to one another by an angle of 90°. The individual membranes are joined to one another at their margins and/or at each elevated part. Methods which may be used are those such as adhesive bonding (for example UV adhesives), ultrasound welding, heat welding, bonding or the formation of covalent molecular bonds (for example $NH_3$—COOH to form an amide bond).

The membrane stacks may contain either identical or different membranes with regard to the structuring or composition thereof. In a preferred embodiment, the membrane stacks consist of structured, permeable, non-porous membranes in an alternating sequence with nanoporous membranes. The membrane stack preferably consists of approx. 10, preferably approx. 50, more highly preferably approx. 100 and still more preferably more than approx. 100 membranes, for example even more than 1000 membranes.

The critical component of the gas transfer device according to the invention with regard to its useful life is the membrane. Previous, wide-ranging clinical use of organ-assisting systems with foreign surfaces which come into contact with blood has shown that unwanted systemic reactions (proinflammatory immune response) may occur. Over long-term use of conventional blood contact surfaces, the attachment of plasma proteins and cells results in a reduction in cross-section and thrombosis. In addition, long-term use brings about the formation of a proliferative internal layer, known as the "neo-intima". This phenomenon is in particular observed in oxygenators, which are used to assist lung function, for example in heart-lung machines, but also in artificial heart systems or heart support systems or haemodialysers. The useful life of the membrane thus can and should be improved in various ways.

In one embodiment of the present invention, the membrane may be post-treated by plasma activation.

In a further embodiment of the present invention, in particular for use of the gas transfer device according to the invention in medicine, the membrane may be colonised with cells, preferably epithelial cells. For a gas transfer device according to the invention which is usable over the long-term in a medical context (for example as a lung support system), colonization of the membrane with cells distinctly extends useful life because it prevents or strongly inhibits nonspecific attachment of substances from the media used to the membrane and thus the gas permeability of the membrane is unimpaired or only immaterially so over time.

In still another embodiment of the present invention, the membrane is coated with biological substances, for example selected from (poly)saccharide, preferably heparin, nucleic acid, preferably DNA, RNA or PNA, protein, preferably albumin, lipid, proteoglycan, or organic polymers, for example polyethylene glycol or with combinations of these substances.

In order to colonise the membrane with cells or to coat the membrane with other substances, it may be advantageous or also necessary to modify the surface of the membrane beforehand. Methods for modifying membranes are known from the prior art and may be selected by a person skilled in the art on the basis of the particular application. It may, for example, be necessary to modify the hydrophobicity/hydrophilicity/charge density of the membrane, for example by physical or chemical treatment of the membrane, in order to improve adhesion.

The invention relates to a gas transfer device comprising a membrane structured as described above and also to the use thereof in a gas transfer device.

According to the invention, the term "gas transfer device" includes a gassing or degassing device and a gas exchange device. In a gassing or degassing device, one or more gases pass from one chamber into the other chamber, without any transfer in the reverse direction occurring. In a gas exchange device, in contrast, the same or another gas or also a plurality of gases additionally migrate into the first chamber. The gases are thus exchanged for one another. The quantity of gas which migrates in one direction need not here be identical to the quantity of gas migrating in the opposite direction. Transfer typically occurs in accordance with the particular concentration gradient.

The at least two chambers of the gas transfer device according to the invention serve in each case to receive a medium, i.e. a gas, a liquid or a solid or mixtures thereof. Depending on the field of application for the gas transfer device according to the invention, the chambers serve to receive specific media. In an application for gas purification, a gas to be separated is present in a gas mixture or in a liquid in one of the chambers, a further chamber likewise contains either a gas or a liquid into which the gas to be separated is intended to pass. The latter-stated chamber may, however, also be unfilled or be under a slightly or greatly reduced pressure in order to facilitate gas transfer.

For use in biotechnology, at least one of the chambers preferably serves to receive a liquid, for example a culture medium, and another chamber to receive a gas which is intended to pass over into the liquid. When used as an oxygenator in medicine, the gas transfer device according to the invention comprises at least two chambers, one of the chambers preferably serving to receive a liquid and a further chamber to receive a gas which is intended to pass over into the liquid. If the gas transfer device according to the invention is used for gassing or for gas exchange in blood, at least one chamber receives the liquid, thus for example blood, and at least one further chamber receives oxygen or an oxygen-containing gas mixture. In this case, oxygen from the one chamber passes through the membrane into the chamber filled with blood, and carbon dioxide optionally moves from the chamber filled with blood into the oxygen-containing chamber. Transfer of carbon dioxide into the at least one oxygen-containing chamber may also not occur here by the membrane being selected such that it does not permit carbon dioxide permeability.

Depending on the use of the gas transfer device according to the invention, the chambers may be made from any desired suitable material. For example, the chambers may consist of plastics, metal, glass, ceramics or other materials, for example composite materials. Steel chambers may also be used for reactor applications. The preferred material for the chambers is plastic. It does, however, lie within the discretion of a person skilled in the art to select a suitable chamber material for a specific use of the gas transfer device according to the invention. In this case, the different chambers may be manufactured either from the same material or also from different materials. For a chemical application, it is in particular the stability of the material which is of significance, whereas for use in biotechnology and medicine attention must in particular be paid to compatibility with the media used in the chambers, in particular standards for medical use (sterility etc.) must, for example, be observed.

Likewise depending on the use of the gas transfer device according to the invention, the size of chambers may be selected in suitable manner. The chambers may here be of identical or different sizes and also have identical or different geometries. For instance, one or also more chambers may be of such small dimensions that the membrane is in direct contact with the (opposing) chamber wall (preferably by way of the structuring on the membrane). On the other hand, one or also a plurality of the chambers may have dimensions of up to a few meters. For example, for use as a reactor (for example in chemistry or biotechnology), one of the chambers may itself take the form of a reactor which may, for example, be up to about 10 m in width. In the former case of small chamber dimensions, at least one of the chambers preferably has a diameter of about 1 μm to about 1 cm, more highly preferably about 5 μm to about 500 μm, still more preferably about 10 μm to about 200 μm and most highly preferably about 20 μm to about 100 μm. In the latter case, for example for use as a reactor, at least one of the chambers preferably has a diameter of about 1 cm to about 10 m, more highly preferably about 5 cm to about 5 m, still more preferably about 10 cm to about 2 m and most highly preferably about 20 cm to about 1 m. Particularly preferably, at least two chambers have the above-stated diameter. It does, however, lie within the discretion of a person skilled in the art to specify a size for the chambers of the gas transfer device according to the invention which is suitable for a specific use. This applies likewise to dimensioning the length and height of the chambers.

The chambers of the gas transfer device according to the invention in each case comprise at least one opening to receive the medium. The chambers preferably in each case comprise at least one inlet and one outlet if they are to be take the form of through-flow chambers. Preferably, at least one of the chambers takes the form of a through-flow chamber; more highly preferably, all the chambers are constructed as through-flow chambers. Connections to further chambers or equipment may be provided at the inlets and/or outlets. For example, connections for tubes which serve to introduce media into the chambers and/or to remove the media may be provided at the inlets and/or outlets. If at least two chambers take the form of through-flow chambers, they may be operated co- or countercurrently. Pumps may, for example, be used for passing the media through the chambers. The media may be passed through the chambers at ambient pressure or at reduced or elevated pressure. For example the media could be passed through the chambers at a reduced pressure of 100 to 10 mbar or at an elevated pressure of 50 to 300 mbar.

In one embodiment of the present invention, the gas transfer device according to the invention comprises more than two, preferably more than 10, more highly preferably more than 20, still more preferably more 50, most highly preferably more than 100 chambers, which are in each case separated from one another by a membrane.

The gas transfer device according to the invention is preferably constructed such that the chambers alternately contain the medium which absorbs a gas and that which releases or is a gas.

A gas transfer device according to the invention may furthermore, in an alternative embodiment of the invention, consist of two or more of the stated devices, wherein the chambers are preferably located above one another (i.e. parallel to one another). Alternatively, the chambers may also be arranged concentrically serially or around one another.

In this case too, the chambers containing the medium which absorbs the gas preferably alternate with chambers which contain the gas-releasing medium.

A device comprising more than two chambers ensures greater efficiency than devices with only two chambers. The improved efficiency is achieved at the cost of reduced compactness of the gas transfer device according to the invention.

According to the invention, the gas transfer device is used for gassing or gas exchange in any desired media (gas, liquid, solid, mixtures thereof, etc.).

In chemistry, the gas transfer device according to the invention may in general be used for reactions used in which gases play a role, such as for example gas/gas, gas/liquid or gas/solid reactions. Moreover, the gas transfer device according to the invention may likewise be used for gas purification and gas separation.

The gas transfer device is preferably used in biotechnology and in medicine. In biotechnology, it is in particular used as or in a bioreactor for culturing various cells for example with the aim of expressing genes of interest.

In medicine, the gas transfer device according to the invention is preferably used for gassing blood, in particular in patients with lung failure or other lung disorders for long-term therapy or during surgical operations, for example transplantations during which the patient is connected to a heart-lung machine, for acute therapy.

In one particularly preferred use, the gas transfer device according to the invention may be used for gassing blood or for gas exchange in blood. In this way, it assumes the function of an artificial lung. Such an artificial lung typically takes the form of an external device, but could however also be implanted in a patient. Depending on whether the gas transfer device according to the invention takes the form of an external or implanted device, it has different dimensions. An internally usable gas transfer device according to the invention will accordingly be built on a miniature scale, so that it is in particular suitable for implantation, for example in a patient's vein.

Depending on the use of the gas transfer device according to the invention, the chambers of the gas transfer device may serve to receive different media. For example, a plurality of chambers may be filled with gases. One of the chambers or also all of the chambers may likewise serve to receive a liquid.

For use in medicine or in biotechnology, the liquid is preferably a biological liquid. The biological liquid should be taken to mean not only a liquid which is a bodily fluid of a living organism, but also liquid which is biologically non-toxic for at least one organism or is required for the growth thereof. In one embodiment of the present invention, the biological liquid is selected from the group consisting of blood, blood serum, cell suspension, cell solution and culture medium. If at least one of the chambers of the gas transfer device according to the invention serves to receive a liquid, it is preferred for the membrane which separates this chamber from a further chamber to comprise structuring, as described above, on the liquid side.

As has already been described, the chambers of the gas transfer device according to the invention may be differently dimensioned. The chambers may thus be of very small dimensions and be used as through-flow chambers for example for use in reactors (chemical reactors or bioreactors). They may here be connected, via suitable connections, either internally or also externally to the reactors. For example, a proportion of the medium may be withdrawn from the reactor via suitable connections (for example tubing) and introduced into one of the chambers of the gas transfer device. The other chamber (for example taking the form of a through-flow chamber) may be filled with another medium which releases a gas to the liquid from the reactor or absorbs a gas.

On the other hand, at least one of the chambers may have such large dimensions that it itself serves as a reactor. A medium is then passed through a further chamber, said medium serving to receive or to release a specific gas to the reactor medium.

An example embodiment of an extracorporeal gas transfer device for gassing blood could be produced on the basis of the IL-1000-01 Novalune®-iLA membrane ventilator from Novalung GmbH. This ventilator belongs to the group of extracorporeal gas exchange systems comprising an albumin-heparin coating. Such a ventilator serves to supply oxygen to and remove carbon dioxide from blood bypassed from a patient. The system consists of an "artificial lung", which corresponds to a gas transfer device, and an inlet/outlet line serving to carry the blood to/from the device with a tube extension. This system is non-directional and, thanks to its symmetrical structure, may receive inflow from both sides. The two inlet/outlet lines and tube extensions of the system are made up of the following components:

inlet/outlet elbow to prevent tube kinking
⅜×3/32 inch PVC tube with female quick coupling
tube extension with male/female quick coupling The inlet/outlet elbows serving to carry the blood to/from the device are fitted in the inlet/outlet zone of the membrane lung to prevent tube kinking. The transitions into the inlet/outlet lines and tube extensions are steplessly constructed in order to minimise the risk of thrombosis due to dead zones, sharp edges etc. in the flow region.

The membrane used according to the prior art in the Novalung®-iLA membrane ventilator is a hollow fibre membrane, through which oxygen is released into the blood and carbon [dioxide] removed from the blood. According to the invention, this hollow fibre membrane may be replaced by a structured membrane as defined in the present invention.

The Novalung®-iLA membrane ventilator system functions according to the following principle: blood emerges from the femoral artery via the arterial Novalung® cannula NovaPort® into the feed tube extension and inlet line. The blood passes through the inlet elbow into the membrane lung housing. In the downstream antechamber, the blood is distributed and any incoming air is withdrawn at the top. Deaeration membranes are fitted at the vertex of the membrane system on both sides. These are hydrophobic membranes which allow gaseous substances to pass through, while retaining liquids. The deaeration membranes serve to facilitate filling, deaeration and permanent elimination of air during the method. In the downstream main chamber, gas exchange proceeds as described above.

The decarboxylated and oxygenated blood is supplied to the patient's femoral vein via the outlet elbow, the membrane system, the outlet line with tube extension and the Novalung® cannula NovaPort®.

Further technical details are stated in the following table:

| Technical details: | |
|---|---|
| Blood flow rate | 0.5-4.5 l/min |
| Maximum recommended gas flow rate | 10 l/min |
| Maximum pressure, gas side | 20 mmHg |
| Maximum pressure, blood side | 200 mmHg |
| Surface area of oxygenation membrane | 1.3 m$^2$ |
| Total capacity | 240 ml |

| Peripheral interfaces: | | |
|---|---|---|
| Connection point | Connection ports | Connector size |
| Blood inlet/outlet tube | 2 | 3/8" × 1/32" Quick couplings |
| Gas connectors | 2 | 1/4" |
| Deaeration connectors | 2 | Luer Lock |

The gas transfer device according to the invention may moreover comprise still further components. These include, for example, a housing which may be constructed from any desired material.

Moreover, still further components may be connected to the gas transfer device according to the invention which are required for or have a positive effect on the proper functioning of the gas transfer device. For example, a heat exchanger may be connected to the gas transfer device in order to control the temperature of the medium located in or passed through the chambers. Moreover, apparatuses may likewise be connected to the gas transfer device according to the invention which monitor or predetermine specific parameters of the medium located in or passed through the chambers. For example, an apparatus may be connected to the gas transfer device which monitors gas pressure (when gas is used as the medium).

The invention likewise relates to the use of a structured membrane as described above in an artificial lung or a bioreactor.

BRIEF DESCRIPTION OF THE DRAWINGS

The invention will now be explained with reference to specific exemplary embodiments shown in the attached drawings, identical features being provided with identical reference numerals. In the Figures:

FIG. 6 is a perspective view of a gas transfer device according to a preferred exemplary embodiment of the invention, and FIG. 7 is a graph showing oxygenation in a test liquid in a simple gas transfer device according to an exemplary embodiment of the invention.

DESCRIPTION OF THE EXEMPLARY
EMBODIMENTS OF THE INVENTION

Figure 1:
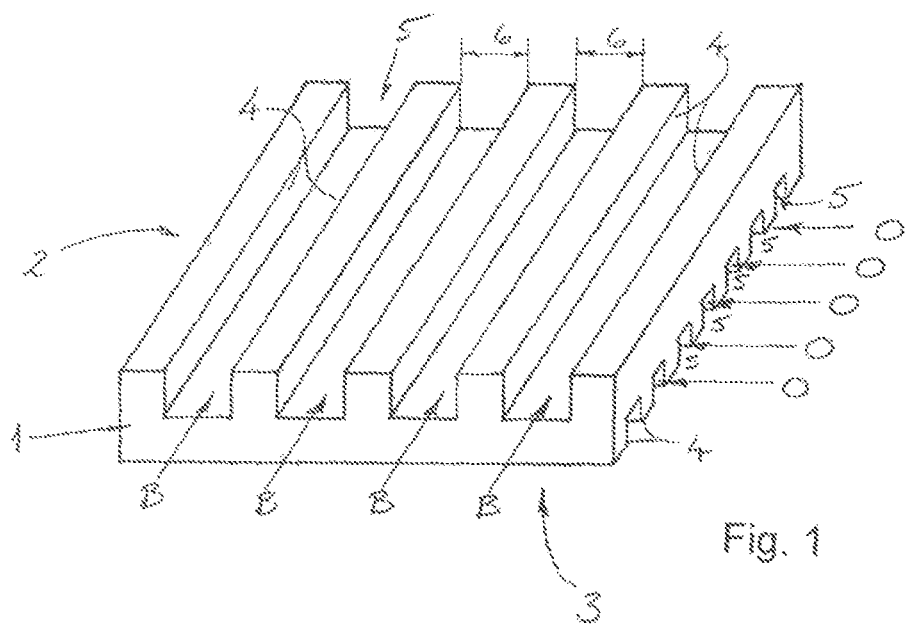
FIG. 1 is a schematic perspective view of a structured membrane for use in a gas transfer device according to a simple exemplary embodiment of the invention.

FIG. 1 shows part of a gas-permeable and liquid-impermeable, structured membrane 1 for use in a gas transfer device according to a simple exemplary embodiment of the invention in schematic and highly magnified form. The two opposing sides 2, 3 of the membrane 1 are provided with a structure and this structure consists of parallel-extending walls 4 which form channels 5 therebetween. The walls 4 are arranged with regular spacing 6 from one another over the two outer faces 2, 3 of the membrane 1 and project substantially perpendicularly upwards and downwards from the plane of the membrane 1. The spacing 6 of the walls 4 in this exemplary embodiment is in the range from approx. 20 to 150 µm and the channels 5 constitute more than 50% of the total surface area 2, 3 of the membrane 1. As may also be inferred from FIG. 1, the channels 5 extend on the upper side 2 of membrane 1 crosswise or at right angles to the channels 5 on the lower side 3 of the membrane.

In a simple gas transfer device according to the invention, at least two chambers are separated from one another by the gas-permeable and liquid-impermeable membrane shown in FIG. 1. On the upper side 2 of the membrane 1, at least one first chamber is formed in part by the membrane 1 and on the lower side 3 at least one second chamber is formed in part by the membrane 1. The at least one first chamber on the upper side 2 of the membrane is intended to receive a biological liquid such as for example blood and the at least one second chamber on the lower side 3 of the membrane is intended to receive a gas such as for example oxygen. Each chamber is furthermore constructed as a through-flow chamber, such that the blood B may flow on top for example from the front to the back and the oxygen O underneath for example from the right to the left through the respective chamber. As described above, the structuring of the membrane surfaces serves to enhance gas transfer by providing a larger area for intimate contact between the liquid and gaseous phases. In addition, however, the flow characteristics of the liquid and gaseous phases over the structuring (for example due to turbulence) may also promote gas transfer through the membrane. Improved mass transfer furthermore arises in particular due to improved diffusion characteristics, which are attributable to the small spacing 6 of the walls 4 and a consequent reduction in flow resistance.

Figure 2:
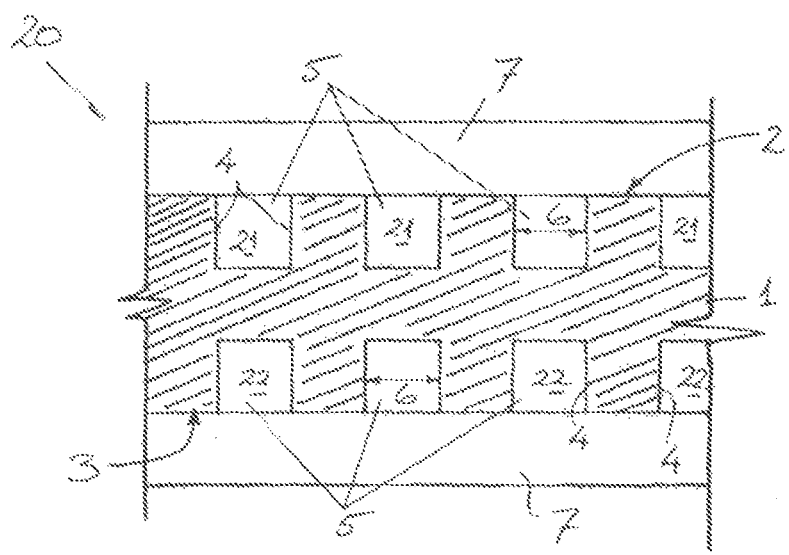
FIG. 2 is a schematic cross-section through part of a gas transfer device according to a simple embodiment of the invention.

FIG. 2 shows a schematic cross-section through part of a gas transfer device 20 according to a simple exemplary embodiment of the invention. In this example, the membrane 1 is strengthened by two layers 7 of a support material. The support material 7 preferably consists of the same polymer as the membrane 1 and is joined thereto by welding (for example by ultrasound or laser) or a covalent bond. Each support layer 7 may have a wall thickness which is the same as or greater than that of the membrane 1, for example a distinctly greater wall thickness of up to 1 mm or 2 mm. As is clearly evident from FIG. 2, the channels 5 on the upper side 2 of the membrane 1 form, together with the upper support layer 7, a row of first chambers 21, arranged next to one another, for the biological liquid (blood). In identical manner, the channels 5 on the lower side 3 of the membrane 1 form, together with the lower support layer 7, a row of second chambers 22, arranged next to one another, for the gas (oxygen). In this example, the channels 5 on the upper and lower sides 2, 3 of the membrane 1 extend parallel to one another, but the blood B and oxygen O nevertheless flow in opposite directions. On the upper side 2, the blood B flows, for example, through the first chambers 21 into the plane of the drawing, as viewed by the observer, and on the lower side the oxygen O flows through the second chambers 22 out of the plane of the drawing.

Figure 3:
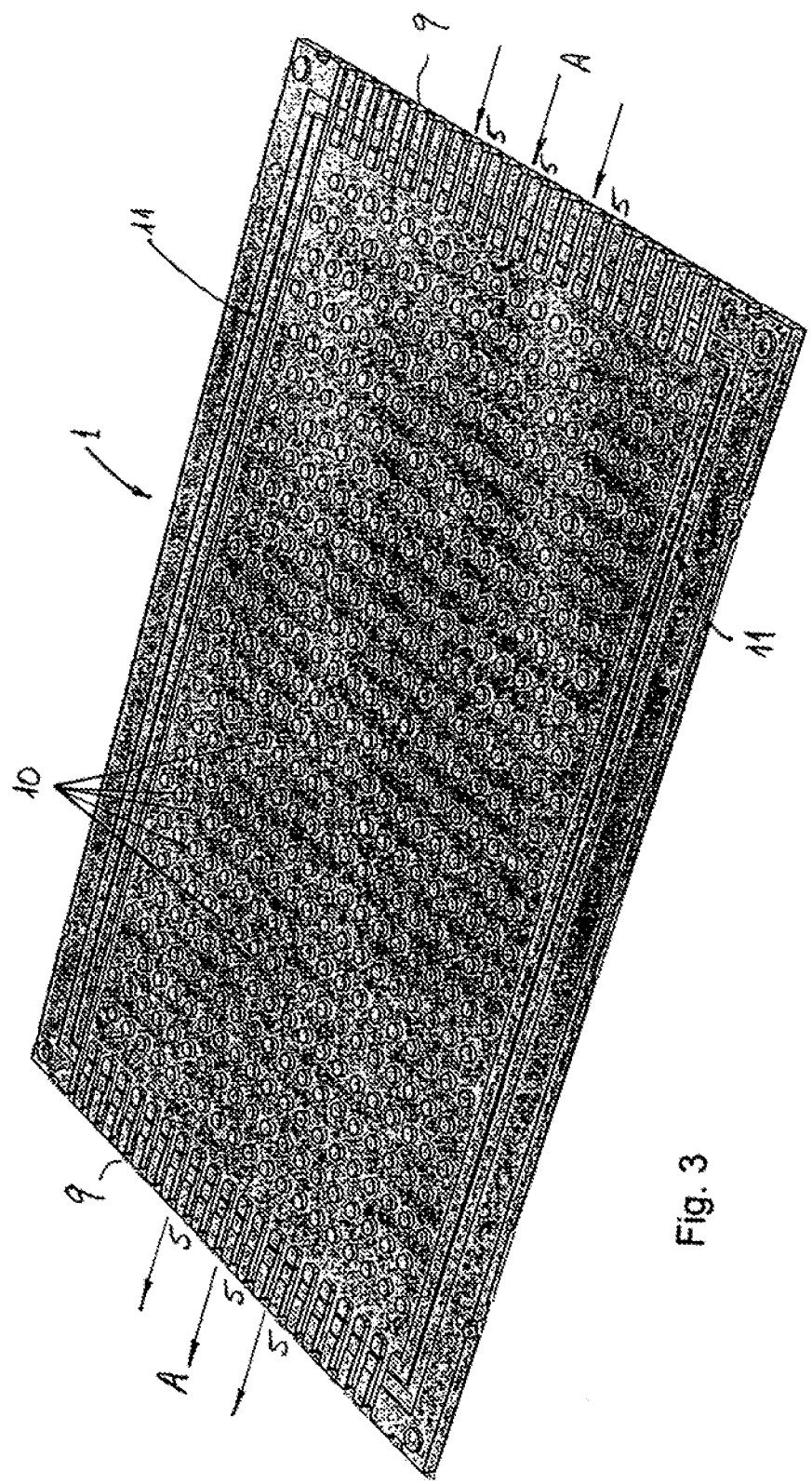
FIG. 3 is a perspective view of a structured membrane for use in a gas transfer device according to a preferred exemplary embodiment of the invention.
Figure 4:
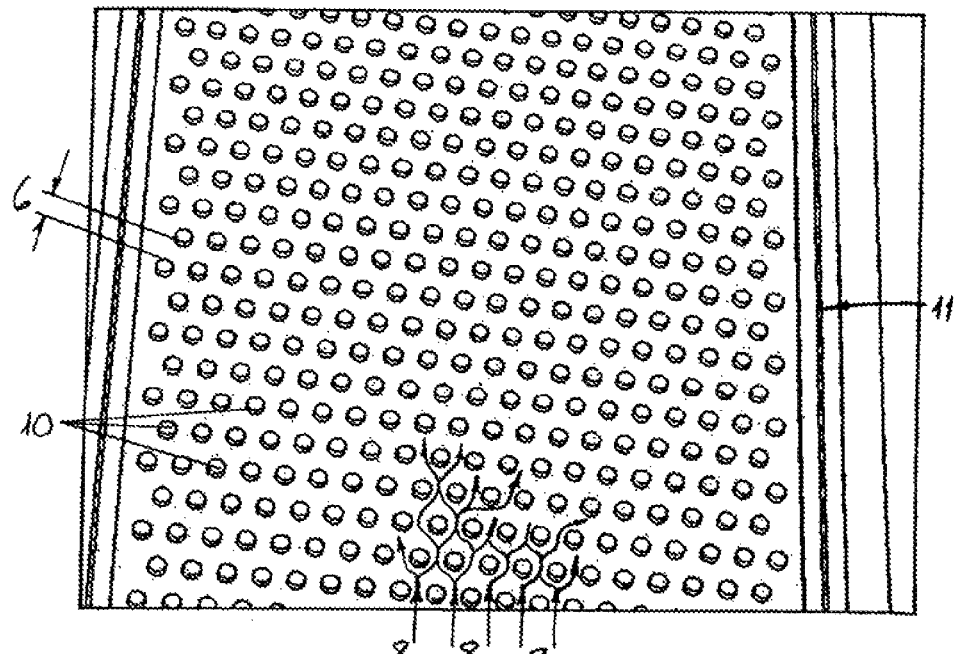
FIG. 4 is a perspective view of part of the structured membrane shown in FIG. 3.
Figure 5:
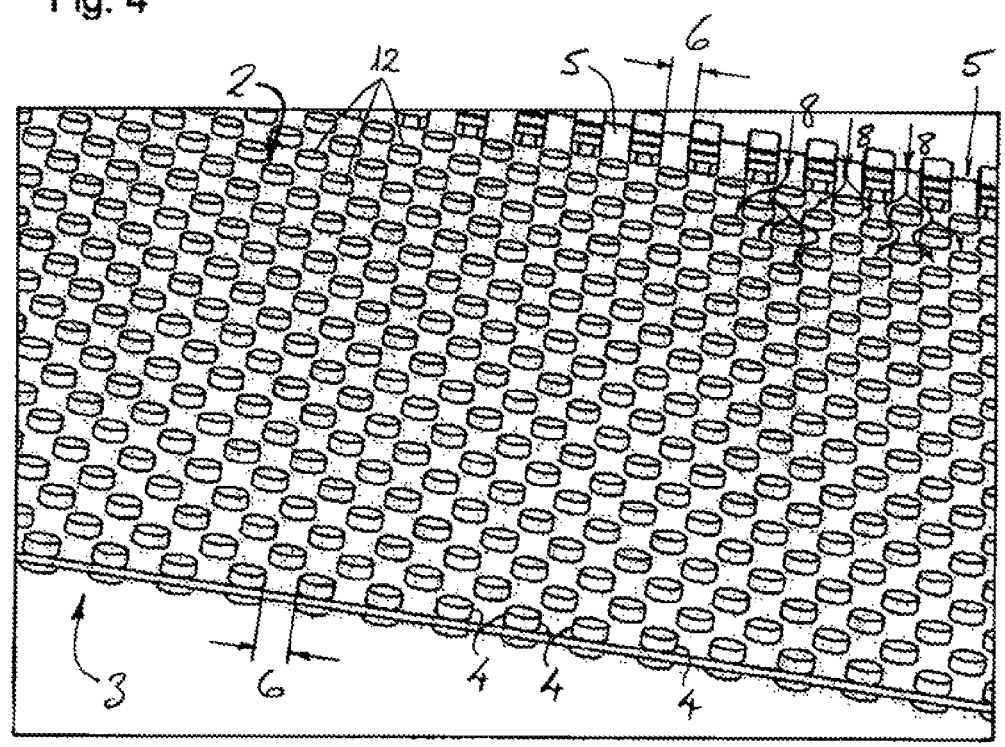
FIG. 5 is a further perspective view of part of the structured membrane shown in FIG. 3.

A structured membrane 1 for use in a gas transfer device 20 according to a preferred exemplary embodiment of the invention will now be described with reference to FIGS. 3 to 5. As is shown FIGS. 3 to 5, again in highly magnified form, this membrane is structured such that it forms both straight channels 5 and branching structures or branching or branched pathways 8 for through-flow of the liquid and gaseous phases. In these figures, it is primarily only the upper side 2 of the membrane which is visible, but the lower side 3 is similarly constructed. At the opposing ends 9 are provided parallel-extending square recesses which form a row of channels 5 arranged next to one another, for example for a biological liquid. These channels 5 belong to the first chamber 21 and form inlets 23 into or outlets 24 out of the first chamber 21 with the direction of flow shown by the arrows A. The channels 5 communicate with a wide, central field on the upper side 2 of the membrane, which is provided with cylindrical projections or bumps 10 which project substantially perpendicularly out of the plane of the membrane. As may be discerned from FIG. 5, the lower side 3 of the membrane is of identical appearance. The walls 4 of the channels 5 and the projections or bumps 10 are all at a distance 6 from one another in the range from approx. 20 to 150 µm. Furthermore, the projections or bumps 10 are arranged such that they stand as obstructions in the direction of flow and cause deflection and splitting of flow through the respective chamber. This deflection and splitting of flow in turn leads to branching structures 8 in the chamber or, in other words, to branched or branching through-flow pathways 8, as indicated with the flow arrows. Since this membrane 1, as in FIG. 2, is provided and strengthened above and below with a support material 7, the cavities which create the upper first chamber 21 and the lower second chamber 22 are obtained. The support layers 7 are arranged and joined as described above. At the edge of the upper (and lower) side 2 of the membrane there is provided a rectangular recess 11 to receive the support layer 7, if the membrane 1 is lidded from above with this layer 7. The interior side of the support layer 7 may also be in contact and connected with the upper end 12 of the projections or bumps 10, but this is not absolutely necessary. The upper ends 12 of the projections or bumps may also be freestanding in the respective chamber.

FIG. 6 shows a gas transfer device 20 according to a preferred exemplary embodiment of the invention in perspective view. The device 20 consists of a membrane stack. The membranes 1 are similar to those shown in FIGS. 3 to 5, but the inlets 23 and outlets 24 on the lower side 3 are oriented at right angles to those on the upper side 2, as in FIG. 1. A biological liquid such as blood may thus flow in a direction B over the upper side of each membrane 1 and oxygen O in a crosswise direction over the lower side 3 of each membrane 1. Stacking of the individual membranes 1 one on top of the other gives rise to a cuboidal arrangement, which, with corresponding peripheral seals and suitable connections for connecting tubes, serves as a module in a gas transfer device, for example in an artificial lung.

FIG. 7 shows a graph which presents the results from oxygenation of a test liquid in an individual microchannel. The microchannel was provided with a mixer structure (i.e. a winding channel) and had a length of 66 mm and a square cross-section 320 µm in depth and 320 µm in width. The test liquid was pumped through the microchannel at a volumetric flow rate of 2.4 ml/min. The graph reveals considerable oxygenation (as partial pressure in the liquid) after the method using the gas transfer device according to the invention.

As a person skilled in the art will understand, the gas transfer device according to the invention may be constructed differently than in the figures without deviating from the general features of the invention stated in the claims. For example, the second chamber could be located in the first chamber or be substantially surrounded by the first chamber. Alternatively, the first chamber could be located in the second chamber or be substantially surrounded by the second chamber. As a person skilled in the art will also understand, the device according to the invention is not limited to at most one treatment of the biological liquid. Instead, the structure of the device according to the invention permits a plurality of possible simultaneous treatments.

The invention claimed is:

1. A gas transfer device comprising at least two chambers and at least one gas-permeable and liquid-impermeable membrane, wherein the chambers are separated from one another by the membrane(s), and wherein the membrane(s) is/are structured on at least one side and channels and/or branching structures are formed through a corresponding surface of the membrane by this structure, wherein the channels include walls having a spacing of ≤500 µm, and the proportion of the membrane surface area which comprises channels and/or branching structures having this spacing constitutes at least 50% of the total surface area of the membrane.

2. A device according to claim 1, wherein the at least two chambers are formed at least in part by the membrane or by the membrane structure.

3. A device according to claim 1, wherein the walls of the structure on the at least one side of the membrane project or stand out from a plane of the membrane and/or project or extend into one of the chambers.

4. A device according to claim 1, wherein the at least two chambers comprise a first chamber to receive a biological liquid and a second chamber to receive a gas, wherein the channels and/or branching structures formed by the structure serve for the transfer of gas molecules between the first and second chambers.

5. A device according to claim 4, wherein the first chamber is subdivided into a plurality of chambers, such that the device comprises a plurality of first chambers, which are separated from the second chamber by a gas-permeable and liquid-impermeable membrane; and/or wherein the second chamber is subdivided into a plurality of chambers, such that the device comprises a plurality of second chambers which are separated from the first chamber by a gas-permeable and liquid-impermeable membrane.

6. A device according to claim 5, wherein the plurality of first chambers are arranged next to one another in one or more rows, are spaced apart from one another, and/or are arranged one above the other in a plurality of layers.

7. A device according to claim 5, wherein the plurality of second chambers are arranged next to one another in one or more rows, are spaced apart from one another, and/or are arranged one above the other in a plurality of layers.

8. A device according to claim 1, wherein at least one of the chambers is constructed as a through-flow chamber, and/or wherein the first chamber is constructed for through-flow from an inlet to an outlet in a direction contrary or crosswise to the second chamber.

9. A device according to claim 1, wherein the membrane is structured on both sides.

10. A device according to claim 1, wherein the membrane comprises an organic material.

11. A device according to claim 10, wherein the organic material is a polymer, polymer composite or polymer multi-layer.

12. A device according to claim 11, wherein the polymer is a polyolefin.

13. A device according to claim 12, wherein the polyolefin is polymethylpentene.

14. A device according to claim 1, wherein the membrane takes the form of a membrane stack.

15. A device according to claim 1, wherein the membrane is structured by injection moulding or micro-injection moulding or a hot stamping method.

16. A device according to claim 1, wherein the membrane has a thickness of 10 to 100 µm.

17. A device according to claim 16, wherein the membrane has a thickness of 20 to 50 µm.

18. A device according to claim 1, wherein the membrane is substantially selectively permeable to oxygen and/or carbon dioxide.

19. A device according to claim 1, wherein the membrane is impermeable or only slightly permeable to nitrogen.

20. A device according to claim 1, wherein the membrane is strengthened by a support material.

21. A device according to claim 1, wherein the membrane is colonised with cells.

22. A device according to claim 1, wherein the membrane is coated with one or more substances selected from the group consisting of a (poly)saccharide, nucleic acid, and protein.

23. A device according to claim 1, wherein the first chamber has a diameter of 1 µm to 1 cm.

24. A device according to claim 23, wherein a second or further chamber has a diameter of 1 µm to 1 cm.

25. A device according to claim 4, wherein the biological liquid is selected from the group consisting of blood, blood serum, cell suspension, cell solution and culture medium.

26. A device consisting of two or more of the devices of claim 1.

27. The gas transfer device of claim 9 wherein the structure on one side of the membrane includes at least one of channels and projections while the other side of the membrane includes projections.

28. The gas transfer device of claim 14 wherein the membrane stack comprises at least 10 stacked membrane layers.

29. A gas transfer device comprising at least two chambers and at least one gas-permeable and liquid-impermeable membrane, wherein the chambers are separated from one another by the membrane(s), and wherein the membrane(s) is/are structured on at least one side and channels and/or branching structures are formed on the membrane by this structure, wherein the channels include walls having a spacing of ≤500 µm, and the proportion of the membrane surface area which comprises channels and/or branching structures having this spacing constitutes at least 50% of the total surface area of the membrane, wherein a lengthwise orientation of one of the at least two chambers extends crosswise and at right angles to a lengthwise orientation of the other one of the at least two chambers.

30. A gas transfer device for providing functionality of an artificial lung, the gas transfer device comprising:
   at least one gas-permeable and liquid-impermeable membrane; and
   at least a first chamber for receiving blood and a second chamber for receiving an oxygen containing gas mixture, the at least first and second chambers being separated from one another by the membrane(s), the membrane(s) being structured on at least one side and channels and/or branching structures are formed through a corresponding surface of the membrane by this structure, the channels including walls having a spacing of ≤500 µm, wherein the proportion of the membrane surface area which comprises channels and/or branching structures having this spacing constitutes at least 50% of the total surface area of the membrane.

31. A gas transfer device for use in a bioreactor, the gas transfer device comprising:
   at least one gas-permeable and liquid-impermeable membrane; and
   at least a first chamber for receiving a culture medium and a second chamber for receiving a gas, the at least first and second chambers being separated from one another by the membrane(s), the membrane(s) being structured on at least one side and channels and/or branching structures are formed through a corresponding surface of the membrane by this structure, the channels including walls having a spacing of ≤500 µm, wherein the proportion of the membrane surface area which comprises channels and/or branching structures having this spacing constitutes at least 50% of the total surface area of the membrane.

32. A gas transfer device comprising:
   a structured membrane; and
   at least two chambers, the at least two chambers being separated by the structured membrane, the structured membrane being structured on at least one side and channels and/or branching structures are formed in the structured membrane by the structuring, the channels including walls having a spacing of ≤150 µm, and the proportion of the membrane surface area which comprises channels and/or branching structures having this spacing constitutes ≥50% of the total surface area of membrane.

33. The gas transfer device of claim 32 wherein one of the at least two chambers is configured for receiving blood and the other one of the at least two chambers is configured for receiving an oxygen containing gas mixture, the gas transfer device providing functionality of an artificial lung.

34. The gas transfer device of claim 32 wherein one of the at least two chambers is configured for receiving a cultured medium and the other one of the at least two chambers is configured for receiving a gas, the gas transfer device providing functionality of a bioreactor.

* * * * *